(12) United States Patent
Krill et al.

(10) Patent No.: US 9,617,199 B2
(45) Date of Patent: Apr. 11, 2017

(54) PROCESS FOR PREPARING UNSATURATED ESTERS PROCEEDING FROM ALDEHYDES BY DIRECT OXIDATIVE ESTERIFICATION

(71) Applicants: Steffen Krill, Muehltal (DE); Alexander Lygin, Griesheim (DE); Torsten Balduf, Pfungstadt (DE); Rudolf Burghardt, Darmstadt (DE); Andreas Tepperis, Bad Koenig (DE); Matthias Groemping, Darmstadt (DE)

(72) Inventors: Steffen Krill, Muehltal (DE); Alexander Lygin, Griesheim (DE); Torsten Balduf, Pfungstadt (DE); Rudolf Burghardt, Darmstadt (DE); Andreas Tepperis, Bad Koenig (DE); Matthias Groemping, Darmstadt (DE)

(73) Assignee: EVONIK ROEHM GmbH, Darmstadt (DE)

(*) Notice: Subject to any disclaimer, the term of this patent is extended or adjusted under 35 U.S.C. 154(b) by 0 days.

(21) Appl. No.: 15/030,775

(22) PCT Filed: Dec. 5, 2014

(86) PCT No.: PCT/EP2014/076682
§ 371 (c)(1),
(2) Date: Apr. 20, 2016

(87) PCT Pub. No.: WO2015/091018
PCT Pub. Date: Jun. 25, 2015

(65) Prior Publication Data
US 2016/0251301 A1    Sep. 1, 2016

(30) Foreign Application Priority Data
Dec. 20, 2013    (EP) .................... 13198863

(51) Int. Cl.
| C07C 67/39 | (2006.01) |
| B01J 23/02 | (2006.01) |
| B01J 23/89 | (2006.01) |
| B01J 35/00 | (2006.01) |

(52) U.S. Cl.
CPC ............... *C07C 67/39* (2013.01); *B01J 23/02* (2013.01); *B01J 23/892* (2013.01); *B01J 35/0006* (2013.01); *B01J 35/0013* (2013.01); *Y02P 20/582* (2015.11)

(58) Field of Classification Search
None
See application file for complete search history.

(56) References Cited

U.S. PATENT DOCUMENTS 5,969,178 A * 10/1999 Okamoto ............... C07C 45/35
560/208
2010/0249448 A1    9/2010 Suzuki et al.

FOREIGN PATENT DOCUMENTS

| EP | 2 210 664 A1 | 7/2010 |
| JP | 2003048863 A * | 2/2003 |
| JP | 2007296429 A * | 11/2007 |

OTHER PUBLICATIONS

Machine translation for JP2003048863.*
Machine traslation for JP 2007296429.*
International Search Report issued Mar. 23, 2015 in PCT/EP2014/076682 filed Dec. 5, 2014.
European Search Report issued Jun. 25, 2014 in EP 13 19 8863.6 filed Dec. 20, 2013.

* cited by examiner

*Primary Examiner* — Yong Chu
*Assistant Examiner* — Ana Z Muresan
(74) *Attorney, Agent, or Firm* — Oblon, McClelland, Maier & Neustadt, L.L.P.

(57) ABSTRACT

The present invention relates to a process for preparing methyl methacrylate by a direct oxidative esterification of methacrolein with oxygen and methanol, which is conducted in the liquid phase at a pressure of 2 to 100 bar with a gold catalyst. According to the invention, the liquid phase is withdrawn continuously from the reactor and optionally enriched with oxygenous gas, the pH, after the withdrawal, is adjusted to a pH between 5 and 9 by means of addition of a basic solution and this liquid phase is conducted back into the reactor again to an extent of at least 50%.

18 Claims, 1 Drawing Sheet

Schematic process flow diagram
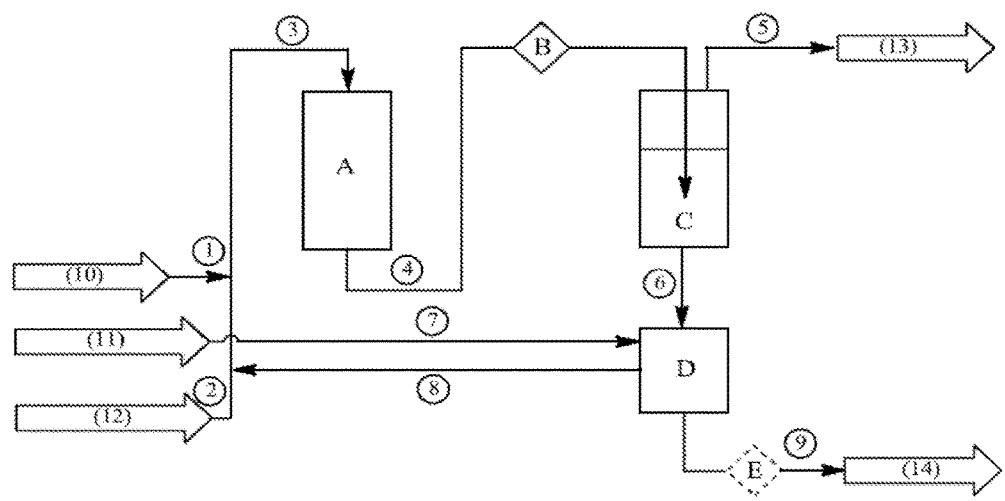

PROCESS FOR PREPARING UNSATURATED ESTERS PROCEEDING FROM ALDEHYDES BY DIRECT OXIDATIVE ESTERIFICATION

FIELD OF THE INVENTION

The present invention relates to a process for preparing methyl methacrylate by direct oxidative esterification of methacrolein.

Methyl methacrylate is used in large volumes for preparation of polymers and copolymers with other polymerizable compounds. In addition, methyl methacrylate is an important synthesis unit for various specialty esters based on methacrylic acid (MAA), which can be prepared by transesterification with the appropriate alcohol.

This results in a great interest in very simple, economically viable and environmentally friendly preparation processes for this starting material.

PRIOR ART

Methyl methacrylate (MMA) is nowadays prepared predominantly proceeding from hydrogen cyanide and acetone via the acetone cyanohydrin (ACH) which forms as a central intermediate. This process has the disadvantage that very large amounts of ammonium sulphate are obtained, and the processing of these is associated with very high costs. Further processes which use a raw material basis other than ACH have been described in the relevant patent literature and have now been implemented on the production scale. In this context, C4-based raw materials such as isobutylene or tert-butanol are nowadays also being used as reactants, which are converted over several process stages to the desired methacrylic acid derivatives.

In general, isobutylene or tert-butanol is oxidized here in a first stage to methacrolein, which is subsequently converted to methacrylic acid with oxygen. The methacrylic acid obtained is subsequently converted with methanol to MMA. Further details of this process are given, inter alia, in Ullmann's Encyclopedia of Industrial Chemistry 2012, Wiley-VCH Verlag GmbH & Co. KGaA, Weinheim, Methacrylic Acid and Derivatives, DOI: 10.1002/14356007.a16_441. pub2.

In a further process, MMA is obtained by oxidation of isobutylene or tert-butanol with atmospheric oxygen in the gas phase over a heterogeneous catalyst to give methacrolein, and subsequent oxidative esterification reaction of methacrolein using methanol. This process, developed by ASAHI, is described, inter alia, in publications U.S. Pat. Nos. 5,969,178 and 7,012,039. A particular disadvantage of this process is the very high energy requirement.

U.S. Pat. No. 5,969,178 describes a process for oxidative conversion of isobutene or tert-butanol to methacrolein and the subsequent oxidative esterification to MMA. In this second stage, a liquid mixture of methacrolein and methanol with reduced water content is reacted with molecular oxygen and a palladium catalyst, the latter usually being present on a support in the form of a palladium-lead catalyst. According to U.S. Pat. No. 6,040,472, a Pd—Pb catalyst of this kind, with an optimal palladium content of 5%, leads to an MMA selectivity of up to 91% and to a space-time yield of 5.3 mol MMA/h*kg of catalyst. However, palladium(-lead) catalysts have the disadvantage that there are high losses of the lead component in continuous operation (called leaching). On the one hand, this leads to costly and inconvenient wastewater disposal; on the other hand, lead salts have to be supplied continuously to the system.

EP 2 177 267 and EP 2 210 664 describe nickel oxide catalysts having a gold content between 1 and 80 mol %, which are initially charged on a support material, for the oxidative esterification of aldehydes to esters. These catalysts are used with a diameter between 10 and 200 μm. More particularly, these particles are present with a shell structure in which the nickel oxide is present on the surface and the gold in an inner layer. These catalysts lead at best to an MMA selectivity of up to 97.1% at a space-time yield of 9.6 mol MMA/h*kg of catalyst.

EP 2 210 664 additionally discloses a specific variant in which catalyst particles in the nanometre range are applied to a support particle having a diameter between 10 and 200 μm. In one variant, this support particle has a size of 3 mm. The catalyst can also be initially charged in cylindrical form or in honeycomb form in a fixed bed reactor. There is no further description of the process regime in such a reactor variant.

EP 1 393 800 describes gold particles or gold-containing particles having a diameter of less than 6 nm on a support material, especially on a metal oxide, as catalyst. Selectivities for MMA of up to 93% and space-time yields of up to 50.7 mol MMA/h*kg of catalyst at a gold content of the catalyst particles of 4.5 mol % are obtained. Beyond that, the disclosure-content is analogous to that of EP 2 210 664.

In addition, the catalyst applied to a support (e.g. $SiO_2$) is used in the form of a suspension catalyst. In suspension catalysis, in an appropriate reactor type, for example a slurry-type reactor, a pulverulent catalyst in solid form is stirred and contacted with the reactants (in this case the aldehyde, the alcohol and an oxygen-containing gas), with mechanical circulation of the mixture and the catalyst subjected to some degree of mechanical stress. Thus, the mixing with the reactants is very good, but there is also discharge of amounts of catalyst or abraded catalyst, and hence faster consumption of the catalyst. Thus, in a similar process in the liquid phase according to JP 06080611A, catalysts have to be recovered by means of a crossflow filtration. At the same time, because of the abrasion, a whole particle spectrum has to be removed, and not just the catalyst grains in their original size and shape. In the filtration of the abraded catalyst material, there is rapid blockage of the filter, and complex control systems have to be installed for backflushing and regeneration of the filters. On the other hand, there is the problem of discharge of the fines or of enrichment in the reaction tank.

According to CN 1931824A, this problem of additional filtration can be solved by initially charging the palladium-lead catalysts on a support material having a diameter between 2 and 5 mm in a fixed bed. In principle, this procedure, however, leads to a reduced space-time yield and other disadvantages.

Methacrylic acid forms as a by-product of the MAL synthesis, and the pH of the reaction mixture falls correspondingly. This leads to further problems. For instance, with falling pH, the 1,1-dimethoxyisobutene (DMI) by-product forms in increasing amounts as the acetal from methacrolein and methanol. Thus, a portion of the methacrolein in the form of the dimethyl acetal is no longer available for further conversion to MMA, and the space-time yield of the MMA synthesis falls correspondingly. Furthermore, the dimethyl acetal presents problems in the subsequent distillative workup of the MMA. Moreover, a mixture having too low a pH adversely affects the stability and lifetime of the catalyst used (leaching, change in the pore structure of the catalyst, etc.). For instance, in relation to the lower limit of pH=5, JP 2003048863 teaches that a basic solution can be added to adjust the pH. This basic solution, for example in the form of an NaOH solution, itself generally has a pH greater than 10.

Slurry-type reactors, which are used according to the prior art particularly for oxidative esterification, are one or more reactors connected in a cascade, wherein circulation is effected with a stirrer. In the reactors, as stated, by monitoring the pH, the addition of the base can be controlled with the aim of maintaining a constant pH. The tank reactor is cooled by means of a heat exchanger, in order to remove the exothermicity of the reaction. Homogeneous heat distribution in the reactor and at the surface of the catalyst—especially in the absence of what are called "hotspots"—is very important for the achievement of high selectivities and for optimal utilization of the catalyst. Gaseous oxygen has to be supplied continuously to the system as a reagent. Because of the explosion risk, oxygen additionally has to be diluted with an inert gas, for example nitrogen. This in turn results in a large gas flow which has to be contacted simultaneously with the liquid while in contact with the catalyst surface. The lower thermal conductivity of gases compared to liquids leads to poorer heat distribution.

In summary, the following aspects of the prior art processes are in need of improvement:
mechanical abrasion of the catalyst
the continuous separation of the reaction mixture from the catalyst
leaching, and the resulting relatively short lifetime of the catalyst
removal of heat, and homogeneous heat distribution in the reactor, or at the catalyst surface
as a result, inter alia, of the named disadvantages, the yield and selectivity of the process.

Problem

In view of the prior art, the problem addressed by the present invention is that of providing a technically improved process for oxidative esterification of methacrolein, which is not afflicted with the disadvantages of conventional processes.

More particularly, prior art processes are to be improved in such a way that less 1,1-dimethoxyisobutene, less Michael adduct and less methacrylic acid is formed in free form during the oxidative esterification of methacrolein. 1,1-Dimethoxyisobutene forms as a by-product particularly in an excessively acidic medium, while the Michael adduct is more likely to form in an excessively basic medium.

In addition, the improved process is to be performable over a long service life, and with simultaneously virtually constant and high selectivities and space-time yields.

In addition, the process is to be performable inexpensively compared to the prior art, more particularly without any great catalyst losses as a result of abrasion or discharge.

Moreover, it should be possible to perform the process with relatively simple and inexpensive plants. The plants should accordingly be associated with low capital costs. At the same time, the plants should be simple to maintain, incur low maintenance costs and be operable safely.

Further problems not mentioned explicitly will become apparent from the overall context of the description and claims which follow.

Solution

The problems are solved by a novel process for preparing methyl methacrylate from methacrolein in a continuous oxidative esterification reaction with oxygen and methanol. According to the invention, this process is conducted in the liquid phase at a pressure of 2 to 100 bar with a heterogeneous catalyst. The heterogeneous catalyst comprises supported gold-containing nanoparticles having a particle size less than 20 nm, preferably between 0.2 and 20 nm. More particularly, the process according to the invention is characterized in that the liquid phase is withdrawn continuously from the reactor and the pH, after the withdrawal, is adjusted by means of addition of a basic solution to a pH between 5 and 9, preferably between 6 and 8.5 and more preferably between 6.5 and 8.0. This withdrawn liquid phase having a pH between 5 and 9 is subsequently conducted back into the reactor to an extent of at least 50%, preferably to an extent of at least 70% and more preferably to an extent of at least 90%.

Such inventive regulation of the pH of the reaction mixture outside the reactor and the at least partial recycling of the mixture into the reactor, compared to the prior art, are a surprisingly simple solution for improving the yield and/or selectivity of the reaction.

The withdrawal of the liquid phase may be continuous, semicontinuous or batchwise, preferably continuous.

At pH values above 9, particularly a Michael addition of the methanol onto the double bond occurs as a side reaction. This too has an adverse effect on the space-time yield and selectivity for MMA. Moreover, a medium having a pH greater than 9 adversely affects the stability and lifetime of the catalyst used (leaching, change in the pore structure of the catalyst, etc.). This is manifested particularly when such a basic solution comes directly into contact with the catalyst. It has been possible to avoid these problems, or reduce them to a minimum, in a surprisingly efficient manner by means of the inventive regulation of the pH.

In a preferred embodiment, the reactor is a fixed bed reactor in which the gold-containing nanoparticles are present on support particles having a total diameter between 0.2 and 20 mm, which are in turn initially charged in the fixed bed. In a fixed bed reactor, the catalyst is immobilized, and the reaction solution generally flows through the reactor from the bottom upward or vice versa. Preferably, no stirrer is required for a fixed bed reactor.

Adjustment of the pH by addition of a basic solution directly to the reactor, as described in the prior art for stirred reactors, is negative for the catalyst service life and selectivity of the reaction in the case of a fixed bed reactor because of the lower degree of mixing of the basic solution with the reaction solution. The result is local differences in the pH, especially close to the introduction site of the basic solution.

It has been found that, surprisingly, it is also possible by means of the inventive process to adjust the pH of the reaction solution for the reaction in a fixed bed reactor and, at the same time, to achieve long catalyst service lives, a high selectivity and very good yields.

Furthermore, it has been found that, surprisingly, the process according to the invention can not only enhance the selectivity by suppressing side reactions, but that it was also possible to increase the space-time yield compared to prior art processes even in reactors having immobilized catalysts. The latter increase is attributable inter alia to a further surprising effect of the process according to the invention. The circulation of a large portion of the liquid phase increases the total supply of dissolved oxygen at the catalyst surface per unit time. This would not be the case if the liquid phase were withdrawn continuously from the reactor and not recycled. In such a process, to achieve the same amounts of dissolved oxygen in the liquid phase, significantly higher partial oxygen pressures (for example in the form of a higher oxygen content in the feed gas mixture) would have to be forced into the reactor. However, because of the potential explosiveness of the reaction mixture and the larger gas phase in such a case, this is associated with high safety risks.

If, on the other hand, in a process without circulation, an increase in the partial $O_2$ pressure should be dispensed with, the oxygen supply per unit time directly at the catalyst will be reduced and the space-time yield will be correspondingly lower. The solubility of oxygen is very low overall. For instance, the mole fraction for 1 atmosphere of $O_2$ pressure at 50° C. in water is $0.17*10^{-4}$, and in methanol is $4.01*10^{-4}$.

In an alternative, likewise preferred embodiment, the gold-containing nanoparticles are present on support particles having a total diameter of less than 0.2 mm. In this embodiment, the reaction is conducted in a stirred reactor, i.e. reactor with stirring apparatus. The catalyst particles here are correspondingly circulated in the reaction solution.

In a further, likewise preferred embodiment, the gold-containing nanoparticles are likewise present on support particles having a total diameter of less than 0.2 mm. In this embodiment, however, the reaction is conducted in a fluidized bed-like apparatus. The catalyst particles here are correspondingly circulated and distributed in a catalyst bed with a liquid stream flowing through it.

Irrespective of the embodiment, the process according to the invention has a multitude of advantages over the prior art:

Abrasion of catalysts is minimized at constant pH and through the choice of supported gold-containing catalyst used, or virtually entirely avoided in the embodiment of a fixed bed reactor. This firstly prolongs the catalyst service life and secondly avoids potential problems in filtration, for example the blockage of the filters.

In the case of the embodiment of the invention in the form of a fixed bed reactor, there is particularly good assurance of temperature control of the exothermic reaction through efficient heat exchange in the process according to the invention.

The adjustment of the pH with a basic solution (pH>9) outside the reactor avoids direct contact of the catalyst with an excessively basic medium, i.e. with a medium having a pH greater than 9, or excessively acidic medium, i.e. having a pH less than 5, as can arise in the case of formation of any great amounts of methacrylic acid. This results in a higher catalyst stability and hence longer lifetime or service life.

In general, the oxidative esterification reaction is conducted at a pressure in the range from 2 to 50 bar and at a temperature in the range from 10 to 200° C. It is especially advantageous in this context to conduct the reaction at a higher pressure than described in the prior art. For workup, an elevated reaction pressure is advantageous, since less cooling energy is surprisingly required. Furthermore, workup is much simpler at elevated pressures, and material losses can be distinctly reduced. These effects can be explained in that methyl methacrylate (MMA), methacrolein (MAL), methanol and the methyl formate by-product are low-boiling components. Preferably, the gaseous and liquid reactants are fed in simultaneously, preferably into the upper part of the reactor in the manner of a trickle bed reactor. Thus, a very narrow, homogeneous distribution of gas and liquid is achieved, which in turn brings about a high selectivity and constant activity of the catalyst.

The remaining gaseous phase can then be removed, for example, prior to the recycling of the liquid phase into the reactor, for example directly upstream of the vessel for pH adjustment, by means of the phase separator.

In addition, the oxidative esterification reaction is preferably effected with a mixture of methanol and methacrolein conducted freshly into the reactor, containing a proportion of methacrolein based on the mixture in the range between 20 and 60% by weight, preferably between 25 and 40% by weight.

In the processes described, in which a proportion of only at least 50%, preferably at least 70% and more preferably at least 90% of the liquid phase is returned to the reactor, the remaining proportion of the liquid phase is sent to a workup for isolation of the MMA obtained.

In an alternative embodiment of the present invention, 100% of the liquid phase is conducted back into the reactor. In this embodiment, liquid phase for further workup is withdrawn continuously, semicontinuously or batchwise elsewhere in the reactor—and not in the circulation system.

In addition, it is preferable to dewater this liquid phase withdrawn continuously from the system, containing primarily methacrolein, MMA and methanol, and to conduct the unconverted, reduced-water methacrolein back into the reactor together with methanol. Details of such a method can be found, for example, in U.S. Pat. No. 7,012,039.

The methacrolein fed to the reactor from a preceding stage or a reservoir vessel can be dewatered by distillation before being fed into the reactor, preferably in the presence of methanol. The thus dewatered MAL-and methanol-containing mixture can then be passed into the reactor. Alternatively, this methacrolein can also be passed directly into the distillation apparatus described for dewatering of the liquid phase withdrawn from the reactor. In this way, one distillation apparatus is sufficient for dewatering of both phases. Details of these aspects of such an embodiment of the invention can be found, for example, in European patent application having reference number EP 13186137, filed 26 Sep. 2013.

Because of the explosion risk, it has been found to be particularly advantageous to conduct the process in such a way that the oxygen concentration in the offgas from the system is less than 8% by volume. This can be established by appropriate regulation of the oxygen content in the gas mixture fed in for oxidative esterification. For this purpose, for example, air can be diluted if required with a further gas which is inert in the reaction, for example nitrogen, carbon dioxide or argon, before it is fed in. It is also possible to provide gas mixtures of such gases and pure oxygen. Preferably, the oxygen content of the offgas is determined continuously by means of a sensor, and the gas composition and/or amount of gas in the feed air is automatically regulated correspondingly.

In addition, it is advantageous in the embodiment of the process according to the invention with a fixed bed reactor to operate this fixed bed reactor with a catalyst bed volume/reactor volume ratio greater than 0.01, preferably 0.1 and more preferably greater than 0.2.

ILLUSTRATIVE DESCRIPTION OF AN EXECUTION OF THE INVENTION

One possible embodiment of the invention having a fixed bed reactor is depicted in FIG. 1. Oxygen or $O_2$-containing gas is fed into the reactor A via line 1, and a methacrolein/methanol solution via line 2. The components are mixed and the resulting heterogeneous gaseous/liquid mixture is fed further via line 3 to the fixed bed reactor A, the temperature of which can be controlled with a jacket. Both the gas/liquid mixture and the individual components can be fed to the reactor from the top or from the bottom. The reactor is filled with the appropriate fixed bed catalyst, and the size of the individual catalyst particles has to be large enough (D>0.2 mm) to avoid pressure buildup in the reactor. At the same time, the catalyst particles should not exceed an optimal maximum size (D<20 mm), in order to increase the contact surface area between the catalyst and the reaction mixture. Preferably, the eggshell catalysts in which the active components are preferably distributed on the surface are used. The reaction mixture is cooled by means of a heat exchanger B and passed onward to the phase separator (gas/liquid separation vessel) C. In this vessel, the liquid phase is separated continuously from the gas phase, preferably at low temperature and elevated pressure. The offgas can either be disposed of or preferably recycled. The liquid phase passes through line 6 into the vessel D, in which the pH is adjusted to a pH between 5 and 9 by addition of an alkaline solution (e.g. sodium hydroxide in methanol) via line 7. A portion of this mixture is removed as product via line 9, while the remainder is conducted back into the reactor A via line 8.

In a particularly preferred variant, not the entire reaction mixture is cooled by means of a heat exchanger (B) downstream of the reactor, but only a portion thereof, which is not recycled into the reactor. In this case (the heat exchanger B is dispensed with), most of the reaction mixture is recycled at a reaction temperature and only a portion thereof is removed as product and cooled by means of a heat exchanger (E).

Instead of a fixed bed reactor, however, it is also possible to use another reactor, for example a stirred reactor. The catalyst particle size is guided by the reactor type. In the case of a slurry-bed reactor, for example, a powder catalyst having particle size <0.2 mm is used.

EXAMPLES

Catalyst Preparation

Catalyst 1 (0.9% Au-1.1% NiO on $SiO_2$—$Al_2O_3$—MgO, 1.16-2.36 mm spheres)

A solution of 37.5 g of aluminium nitrate nonahydrate, 25.6 g of magnesium nitrate hexahydrate and 5.4 g of 60% nitric acid in 100 ml of water was mixed at room temperature with 108 g of an SiO2 support (Fuji Silicia, Cariact Q-10, 1.16-2.36 mm spheres). The mixture was stirred at 50° C. for 24 h, then cooled to room temperature, dried at 130° C. and calcined at 300 to 600° C. for a total of 10 h. 30 g of this $SiO_2$—$Al_2O_3$—MgO support were mixed with 100 ml of water and heated to 90° C. After 15 min, a solution of 1.64 g of nickel nitrate hexahydrate and 530 mg of auric acid ($HAuCl_4$) in 100 ml of water was added at 90° C. within 30 min. After stirring at 90° C. for a further 30 min, the mixture was cooled and the solids were removed, then stirred three times more with 100 ml of fresh water each time at 20° C. for 5 min and filtered off. The catalyst was dried at 105° C. within 10 h and calcined at 450° C. under air within 5 h. The catalyst thus obtained contained, according to ICP analysis (mass spectroscopy with inductively coupled plasma), 1.1% Ni and 0.9% Au. The mean particle size of gold nanoparticles (TEM) was less than 5 nm.

Examples

A plant with continuous addition of an NaOH solution and recycling of a portion of the product mixture was used in the example which follows.

The reaction mixture of methacrolein and methanol (30.9% by weight/69.1% by weight) was adjusted to pH=7 by means of a 1% NaOH solution in methanol. This neutralized mixture was fed at a flow rate of 20.9 g/h, together with an $O_2/N_2$ gas mixture (7% by volume of $O_2$), at 11 bar via a line to a tubular reactor heated to 70° C. by a jacket. The $O_2/N_2$ flow was adjusted such that the proportion of $O_2$ in the offgas was 4% by volume. The reactor contained 15 g of catalyst 1. In the neutralization vessel D, pH=7 was established by means of continuous addition of 1% NaOH solution in methanol. The ratio between the stream recycled via line 8 and the product stream was U/P=0 to 10 (see table). The product was withdrawn at particular run times of the plant (see table) and analysed by GC.

TABLE 1

| No. | Return [%] | Run time [h] | U(MAL) [%] | STY [mol MMA/ kg cat h] | S(MMA) [%] | S(DMI) [%] |
|---|---|---|---|---|---|---|
| 1 | 90.9 | 73 | 70.8 | 4.12 | 97.4 | 0.1 |
|   | 90.9 | 512 | 69.8 | 4.06 | 97.2 | 0.1 |
| 2 | 75 | 70 | 55.4 | 3.33 | 94.3 | 0.6 |
|   | 75 | 250 | 53.2 | 3.20 | 94.1 | 0.6 |
| 3 | 0 | 24 | 34.5 | 2.15 | 90.9 | 5.2 |
|   | 0 | 180 | 32.3 | 2.01 | 84.4 | 11.7 |

As apparent from Table 1, an execution as depicted above allows the DMI content in the product to be kept constant at a low level, and high MMA selectivity and activity of the catalyst to be achieved at a high MAL conversion. In contrast, when no recycling is employed (as in No. 3 in Table 1), a large amount of DMI is formed, the selectivity for MMA is correspondingly lower, and the STY (space-time yield) of the catalyst falls.

DRAWING INDEX (A) reactor
(B) heat exchanger
(C) phase separator
(D) vessel for adjustment of pH
(E) alternative or additional heat exchanger
(1) feed of the $O_2$-containing gas mixture (10)
(2) feed of the mixture of methacrolein and methanol (12)
(3) line for mixing of the liquid phase (12) and the gas phase (10) for introduction into the reactor (A)
(4) line for transfer of the withdrawn liquid phase from reactor (A) into the phase separator (C) via the heat exchanger (B)
(5) outlet for the offgas (13) from phase separator (C)
(6) line for the liquid phase from phase separator (C) into vessel (D)
(7) feed of the basic solution (11) for pH adjustment into vessel (D)
(8) recycling of the pH-adjusted liquid phase from vessel (D) back into reactor (A) via line (3) and with enrichment (1) with oxygen from gas mixture (10)
(9) removal of the MMA-containing product stream (14) for further workup

The invention claimed is:
1. A process for preparing methyl methacrylate, comprising:
reacting methacrolein in a continuous oxidative esterification with oxygen and methanol which is conducted in a liquid phase in a reactor at a pressure of 2 to 100 bar in the presence of a heterogeneous catalyst comprising gold-containing nanoparticles having a particle size less than 20 nm;

withdrawing continuously the liquid phase from the reactor and adjusting the pH after the withdrawal to a pH between 5 and 9 by addition of a basic solution outside of the reactor; and conducting at least 50% of the withdrawn liquid phase having a pH between 5 and 9 back into the reactor, wherein the methacrolein is dewatered by distillation in the presence of methanol before being fed into the reactor.

2. The process according to claim 1, wherein at least 70% of the withdrawn liquid phase having a pH between 5 and 9 is conducted back into the reactor.

3. The process according to claim 1, wherein at least 90% of the withdrawn liquid phase having a pH between 5 and 9 is conducted back into the reactor.

4. The process according to claim 1, wherein the gold-containing nanoparticles are present on support particles having a total diameter between 0.2 and 20 mm, and wherein the reactor is a fixed bed reactor.

5. The process according to claim 1, wherein the gold-containing nanoparticles are present on support particles having a total diameter between 0.2 and 20 mm, and wherein the reactor comprises a stirring apparatus.

6. The process according to claim 1, wherein the oxidative esterification reaction is conducted at a pressure in the range from 2 to 50 bar and at a temperature in the range from 10 to 200° C.

7. The process according to claim 1, wherein a feed mixture of methanol and methacrolein passed into the reactor prior to the reacting has a proportion of methacrolein, based on the mixture, in the range between 20 and 60% by weight.

8. The process according to claim 1, wherein a residual proportion of the liquid phase withdrawn continuously from the reactor which is not conducted back into the reactor is dewatered to form a reduced-water mixture containing methacrolein and methanol which is passed back into the reactor.

9. The process according to claim 1, wherein 100% of the withdrawn liquid phase is conducted back into the reactor, and wherein a product liquid phase for further workup is withdrawn continuously, senaicontinuously, or batchwise elsewhere from the reactor.

10. The process according to claim 1, wherein an offgas from the reactor has an oxygen content of less than 8% by volume.

11. The process according to claim 1, wherein the pH of the liquid phase conducted back into the reactor is between 6 and 8.5.

12. The process according to claim 1, wherein the reactor is operated with a catalyst volume to reactor volume ratio greater than 0.2.

13. The process according to claim 1, wherein the methyl methacrylate prepared in the reactor has a 1,1-dimethoxy-isobutene content of less than 0.6%.

14. The process according to claim 1, wherein the catalyst has a space-time-yield of greater than 3.20.

15. The process according to claim 1, which has a methyl methacrylate selectivity of greater than 94%.

16. The process according to claim 1, which has a methacrolein conversion of greater than 53%.

17. The process according to claim 1, wherein the gold-containing nanoparticles are present on support particles having a total diameter between 0.2 and 20 mm, and wherein the reactor is a fluidized bed reactor.

18. The process according to claim 4, wherein the support particles comprise at least one selected from the group consisting of $SiO_2$, $Al_2O_3$, and MgO.

* * * * *